(12) United States Patent
Wolf

(10) Patent No.: US 6,844,166 B1
(45) Date of Patent: Jan. 18, 2005

(54) RECOMBINANT REDUCED VALENCY CARBOHYDRATE BINDING LIGANDS

(75) Inventor: David E. Wolf, Hudson, MA (US)

(73) Assignee: Sensor Technologies Inc., Shrewsbury, MA (US)

( * ) Notice: Subject to any disclaimer, the term of this patent is extended or adjusted under 35 U.S.C. 154(b) by 0 days.

(21) Appl. No.: 09/394,265

(22) Filed: Sep. 10, 1999

Related U.S. Application Data

(60) Provisional application No. 60/099,895, filed on Sep. 11, 1998.

(51) Int. Cl.[7] .......................................... G01N 33/537
(52) U.S. Cl. ...................... 435/7.93; 435/7.1; 435/7.92; 435/14; 436/501; 436/14; 436/147; 436/164; 436/172; 436/95; 436/531; 436/545; 436/546; 436/805; 436/807; 436/815; 436/827
(58) Field of Search .......................... 436/14, 164, 147, 436/172, 95, 501, 531, 545, 546, 805, 807, 815, 827; 435/7.2, 7.92, 7.93, 14, 7, 7.1; 424/9.6, 9.8

(56) References Cited

U.S. PATENT DOCUMENTS

| | | | |
|---|---|---|---|
| 4,041,932 A | 8/1977 | Fostick | 128/2 G |
| 4,071,020 A | 1/1978 | Pugliese | 128/2 A |
| 4,330,299 A | 5/1982 | Cerami | 23/230 B |
| 4,344,438 A | 8/1982 | Schultz | 128/634 |
| 4,401,122 A | 8/1983 | Clark, Jr. | 128/635 |
| 4,822,746 A | 4/1989 | Walt | 436/528 |
| 4,868,103 A | 9/1989 | Stavrianopoulos et al. | 435/5 |

(List continued on next page.)

FOREIGN PATENT DOCUMENTS

| | | |
|---|---|---|
| EP | 0 561 653 A1 | 9/1993 |
| WO | WO 90/10861 | 9/1990 |
| WO | WO 96/36275 | 11/1996 |

OTHER PUBLICATIONS

Cho et al., Galectin-1: Oligomeric structure and interactions with polylactosamine, Trends in Glycoscience and Glycotechnology, 9(45): 47–56 (Jan. 1997), Abstract.*

Lakowicz et al., Optical Sensing of glucose using phase modulation fluorimetry, Analytica Chimica Acta 271: 155–164 (1993).*

Mandal et al., Differences in the binding affinities of dimeric con A and tetrameric con A with large oligomannose–type glycoproteins, Biochemistry 32(19): 5116–5120 (May 1993).*

Stubbs et al., Production of pea lectin in E. coli, Journal of Biological Chemistry, 261(14): 6141–6144 (1986), Abstract.*

Cunningham, Bruce A., et al., "Isolation and Proteolytic Cleavage of the Intact Subunit of Concanavalin A," Biochemistry, vol. 11, No. 17, pp. 3233–3239, (1972).

Gunther, Gary R., et al., "Concanavalin A Derivatives with Altered Biological Activities," Proc. Nat. Acad. Sci. USA, vol. 70, No. 4, pp. 1012–1016, Apr. 1973.

Wang, John L., et al., "Binding and Functional Properties ofConcanavalin A and Its Derivatives," The Journal of BiologicalChemistry, vol. 253, No. 9, p. 3000–07 (1978).

Tanaka, Isao, et al., "Monovalent Monomer Derivative of Concanavalin A Produced By Photochemically Induced Alkylation," J. Biochem, 89, pp. 1643–1646 (1981).

(List continued on next page.)

Primary Examiner—Christopher L. Chin
Assistant Examiner—Gailene R. Gabel
(74) Attorney, Agent, or Firm—Fish & Richardson P.C., P.A.

(57) ABSTRACT

The invention is based on the discovery of reduced valency carbohydrate binding ligands (CBLs) that can be used to to detect or quantitate (i.e., evaluate) carbohydrates in a sample. CBLs can be used with fluorescence resonance energy transfer (FRET) to evaluate free carbohydrates or those within a carbohydrate containing compound.

12 Claims, 3 Drawing Sheets

U.S. PATENT DOCUMENTS

| | | | |
|---|---|---|---|
| 4,981,779 A | 1/1991 | Wagner | 435/288 |
| 5,001,051 A | 3/1991 | Miller et al. | 435/6 |
| 5,028,787 A | 7/1991 | Rosenthal et al. | 250/341 |
| 5,101,814 A | 4/1992 | Palti | 128/635 |
| 5,143,066 A | 9/1992 | Komives et al. | 128/634 |
| 5,244,636 A | 9/1993 | Walt et al. | 422/82.07 |
| 5,320,814 A | 6/1994 | Walt et al. | 422/82.07 |
| 5,326,531 A | 7/1994 | Hahn et al. | 422/82.06 |
| 5,341,805 A | 8/1994 | Stavridi et al. | 128/633 |
| 5,342,789 A | 8/1994 | Chick et al. | 436/501 |
| 5,460,971 A | 10/1995 | Gottlieb | 436/68 |
| 5,628,310 A | 5/1997 | Rao et al. | |
| 6,232,130 B1 | 5/2001 | Wolf | |

OTHER PUBLICATIONS

Schultz, Jerome S., et al., "Affinity Sensor: A New Technique for Developing Implantable Sensors for Glucose and Other Metabolites," *Diabetes Care*, vol. 5, No. 3, pp. 245–253 (1982).

Wilson, T., "Standard Oil patents probe potentially more selective than radioisotope tracers," *BioTechnology Newswatch*, pp. 3 and 4, (1983).

Parker, J.W., et al., "Glucose/Oxygen sensor," Proceedings of SPIE—The International Society for Optical Engineering, vol. 713 Optical Fibers in Medicine II, pp. 113–120 (1986).

Heller, M.J., et al., "Fluorescent Energy transfer Oligonucleotide Probes, Federation Proceedings, Federation of American Societies for Experimental Biology," vol. 46, No. 6, Abstract No. 248, May 1, 1987.

Morrison, Larry E., "Solution Hybridization Measurements Using Complementary Strands of Fluorescent DNA," Gene Probe Technology II, The San Diego Conference (1 pg) (Nov. 4–6, 1987).

Meadows, et al., "Fiber–Optic Biosensors Based on Fluorescence Energy Transfer," *Talanta*, vol. 35, No. 2, p. 145–150 (1988).

Cardullo, Richard A., et al., "Detection of Nucleic Acid Hybridization By Nonradiative Fluorescence Resonance Energy Transfer," *Proc. Natl. Acad. Sci. USA*, vol. 85, pp. 8790–8794 (1988), Biochemistry.

Cardullo, R.A., et al., "Synthesis, Purification, and Characterization of 2,4,6–Trinitrophenyl–UDP–galacatose; A Fluorescent Substrate for Galactosyltransferase," *Analytical Biochemistry*, vol. 188, pp. 305–309 (1990).

Chien, Cheng–Ting, et al., "The Two–Hybrid System: A Method to Identify and Clone Genes for Proteins that Interact with a Protein of Interest," *Proc. Natl. Acad. Sci., USA*, vol. 88, pp 9578–9782 (1991), Biochemistry.

McKinnon, Christine A., et al., "Cross–Linking a Maturation–Dependent Ram Sperm Plasma Membrane Antigen Induces the Acrosome Reaction," Molecular Reproduction and Development vol. 29, pp. 200–207 (1991).

Kroschwitz Jacqueline I., ed., "Biosensors," *Kirk–Othmer Encyclopedia of Chemical Technology*, vol., 4, pp. 208–220 (1992).

Lakowicz, Joseph R., "Fluorescence Lifetime Sensing," *Laser Focus World*, vol., 28, No. 5, pp. 60–62, 66–68, 70, 72, 75, 77–78 and 80, (1992).

Naismith, James H., et al., "Refined Structure of Cadmium–substituted Concanavalin A at 2.0 A Resolution," *Acta Crystallographica*, D49, pp. 561–571 (1993).

Oda et al., "Studies on the Specific Interaction of Concanavalin A and Saccharides by Affinity Chromatography. Application of Quantitative Affinity Chromatography to a Multivalent System" *J. Biochem.*, 89:285–296 (1981).

Becker and Reeke, "Specific Carbohydrate Binding By Concanavalin A and Favin" *Transactions of the ACA*, 25:37–50 (1989).

Saito et al., "A Role of Valency of Concanavalin A and Its Chemically Modified Derivatives in Lymphocyte Activation" *J Biol. Chem.*, 258:7499–7505 (1983).

Schwarz et al., "Thermodynamics of Monosaccharide Binding to Concanavalin A, Pea (*Pisum sativum*) Lectin, and Lentil (*Lens culinaris*) Lectin" *J. Biol. Chem.*, 268:7668–7677 (1993).

* cited by examiner

RECOMBINANT REDUCED VALENCY CARBOHYDRATE BINDING LIGANDS

This application claims benefit of U.S. Ser. No. 60/099,895, a provisional application filed Sep. 11, 1998.

BACKGROUND OF THE INVENTION

This field of the invention is analyte detection.

SUMMARY OF THE INVENTION

The invention is based on the discovery of reduced valency carbohydrate binding ligand (CBLs) that can be used to detect or quantitate (i.e., evaluate) carbohydrates in a sample. CBLs can be used with fluorescence resonance energy transfer (FRET) to evaluate free carbohydrates or those within a carbohydrate containing compound.

Accordingly, one aspect of the invention features methods for evaluating a carbohydrate in a sample. The method can be carried out by contacting a reduced valency CBL with the carbohydrate in the sample and with a glycoconjugate that includes the carbohydrate. The extent or degree to which the reduced valency CBL binds the glycoconjugate is correlated with the amount of the carbohydrate in the sample. The reduced valency CBL and the glycoconjugate may bind reversibly. Thus, the amount of carbohydrate in the sample is quantitated by determining the extent to which the carbohydrate occupies the reduced valency CBL or displaces the glycoconjugate from the reduced valency CBL (see FIG. 3).

In the methods described herein, either the reduced valency CBL or the glycoconjugate, or both, can be labeled. The label can be a detectable label such as, for example, a radioactive label (e.g., a radioisotope), a fluorescent label, an enzyme (e.g., an enzyme the activity of which results in a change in a detectable signal, e.g., a change in color or emission, e.g., fluorescence), a proximity-based signal generating label (e.g., a FRET component), a homogeneous time resolved fluorescence (HTRF) component, a luminescent oxygen channeling assay (LOCI) component, biotin, avidin, or another functionally similar substance, an antibody (e.g., a primary or a secondary antibody), or a portion thereof (e.g., an antigen binding portion of an antibody). In addition, any method of measurement (e.g., fluorescence measurement) described in WO 94/00602 or U.S. Ser. No. 07/905,729 filed Jun. 29, 1992, hereby incorporated by reference in their entirety, can be used with methods and devices described herein.

The methods described herein can be carried out with a sample obtained from the body of a human or other animal (e.g., it can be a sample of urine, blood; plasma, or saliva, or an intracellular, extracellular or interstitial fluid). The sample can also be a cellular homogenate or extract. The carbohydrate of interest within such samples (i.e., the analyte) can be a monosaccharide, a disaccharide, a polysaccharide, glucose, a carbohydrate that is a component of another molecule or a supramolecular structure (e.g., a macromolecule). For example, the analyte can be the carbohydrate moiety of a glycoprotein.

The glycoconjugate can include one or more glycosylated serum albumin molecules, preferably of human or bovine origin, that are capable of binding to reduced valency CBLs. Such glycoconjugates are useful in methods carried out in vivo or ex vivo.

The reduced valency CBL can be a lectin (e.g., a reduced valency Concanavalin A or a modified monomer of Concanavalin A). A monomer that has been modified by a change of at least one amino acid residue is defined as a single subunit (i.e., it is not part of a dimer, tetramer or any higher order structure of Concanavalin A, unless otherwise stated). The reduced valency CBL can be a dimer that includes two modified Concanavalin A subunits. The subunits have been modified by a change of at least one amino acid residue such that the two subunits of the dimer do not form a tetramer or any higher order structure of Concanavalin A, unless otherwise stated.

The reduced valency CBL and the glycoconjugate used in the methods described herein bind reversibly over one or more of the following: the range of carbohydrate concentrations found in body fluids (i.e., urine, cerebrospinal fluid, interstitial fluid); the range of physiological concentrations of carbohydrate in the body fluid being tested; and the range of 0.05 mg/ml to 5.0 mg/ml (e.g., 0.5 mg/ml) of a carbohydrate (e.g., glucose).

The reduced valency CBL and the glycoconjugate (i.e., the specific binding pairs described herein) can be administered to a subject in numerous ways. For example, a specific binding pair can be: placed in a microdialysis tube or vessel; encapsulated; or mixed with a carrier (e.g., an oil into which analytes, such as glucose, can pass). These formulations can be administered, alone or in combination, to a subject. For example, the specific binding pair can be implanted (e.g., subcutaneously implanted) into a subject (e.g., a human patient). The binding pair can also be injected into the subject or tattooed onto the subject's skin. One or both of the components of the specific binding pair can be chemically modified to enable them to bind to the cells of the subject. Specific binding pairs can also be bound to solid supports which are then implanted into the subject such that the support retains the specific binding pair at a desired location. Even in the event the support bearing a binding pair is not implanted, one or both members of the pair can be placed thereon (i.e., adhered to). A non-implantable support can then be contacted (even repeatedly) with samples of body fluids obtained from a subject. The support for the reduced valency CBL, the glycoconjugate, or the specific binding pair can include a membrane that covers the reduced valency CBL, the glycoconjugate, or the specific binding pair and that has a pore size that prevents carbohydrates to pass from a sample to the support.

Preferably, specific binding pairs destined for implantation within a subject are encapsulated (e.g., in a microcapsule) that substantially isolates the pair from the subject's immune system. For example, a specific binding pair can be encapsulated in a hydrogel core (e.g., an alginate or agarose core that is surrounded by an immunoisolating membrane such as a polyamino acid membrane (e.g., a polylysine membrane)). Composite microcapsules such as those described in PCT/US96/03135 are particularly useful with the sensors and methods described herein.

In preferred embodiments, the specific binding pair is illuminated, and the energy transfer (for example, between the first and second energy absorbing FRET components described below) is monitored (e.g., through the subject's skin).

In another aspect, the invention features a method for evaluating a carbohydrate in a sample that is carried out by first contacting the sample with a specific binding pair that includes a first binding member and a second binding member. The first binding member includes a reduced valency CBL coupled to a first energy absorbing FRET component, and the second binding member is a glycoconjugate that includes a carbohydrate and a second energy absorbing FRET component. The excited state energy level of the first energy absorbing FRET component overlaps with the excited state energy level of the second energy absorbing FRET component, and the reduced valency CBL and the glycoconjugate can reversibly bind to each other such that carbohydrate present in the sample can displace the glycoconjugate and reversibly bind to the reduced valency CBL. The extent to which non-radiative fluorescence resonance energy transfer occurs between the first energy absorbing FRET component and the second energy absorbing FRET component is then evaluated. This evaluation reflects the presence of carbohydrate in the sample and correlates with its amount. The evaluation can be made in the presence of the glycoconjugate displaced by the carbohydrate and the reduced valency CBL reversibly bound to the carbohydrate.

Energy transfer can be evaluated in numerous ways. For example, it can be evaluated by measuring one or more of: donor quenching, donor lifetime (e.g., a decrease in donor excited lifetime), sensitized acceptor emission, or fluorescence depolarization. It can also be measured by determining the ratio of two parameters, such as the ratio of: a donor parameter to an acceptor parameter (e.g., the ratio of donor to acceptor fluorescence, or depolarization of fluorescence relative to excitation); a donor parameter to a donor parameter (e.g., the ratio of donor to donor fluorescence, or depolarization of fluorescence relative to excitation); an acceptor parameter to an acceptor parameter (e.g., the ratio of acceptor fluorescence or depolarization of fluorescence relative to excitation). For example (and regardless of whether the method is carried out ex vivo, as described above, or in vivo, as described below) the evaluation can include measuring energy transfer as a function of fluorescence intensities of the first energy absorbing FRET component and the second energy absorbing FRET component. The evaluation can also include a comparison between the extent to which non-radiative fluorescence resonance energy transfer occurs between the first and second energy absorbing FRET components and a FRET value obtained from a calibration step.

In the event the detectable label is a homogeneous time resolved fluorescence (HTRF) component, the evaluation will include measuring energy transfer as a function of fluorescence intensities of a first and second energy absorbing HTRF component. Similarly, in the event the detectable label is a luminescent oxygen channeling assay (LOCI) component, the evaluation will include measuring energy transfer as a function of the photochemical reaction of a first energy absorbing LOCI component and a second chemiluminescence-producing LOCI component.

In preferred embodiments, either the first or second energy absorbing FRET component is a fluorophore (e.g., fluorescein, rhodamine, BODIPY, a cyanine dyes, or a phycobiliprotein). For example, a reduced valency CBL can be labeled with a fluorophore, and the glycoconjugate can be labeled with a fluorophore in the non-radiative fluorescence resonance energy transfer process. A reduced valency CBL can also be labeled with a fluorophore that is the acceptor and the glycoconjugate can be labeled with a fluorophore that is the donor in the non-radiative fluorescence resonance energy transfer process. For example, the first member of a specific binding pair can be fluorophore-labeled reduced valency Concanavalin A, and the second member of the specific binding pair can be fluorophore-labeled glycosylated serum albumin that binds to reduced valency Concanavalin A. Here, the non-radiative fluorescence resonance energy transfer can be determined by measuring the ratio of the light emissions attributable to the two fluorophores.

In another aspect, the invention features an in vivo method for evaluating a carbohydrate (e.g., glucose) in a subject. The method can be carried out by placing a first binding member and a second binding member (i.e., a sensor) in contact with the carbohydrate in the body fluids of the subject (e.g., the sensor can be introduced into an organ or vessel where it would be exposed to glucose). Once in place, the presence and/or amount of the carbohydrate can be monitored without further invasive procedures. For example, a sensor can be placed in, on, or under the subject's skin and glucose can be evaluated by illuminating the sensor at the excitation wavelength of, e.g., an energy absorbing FRET donor. Energy transfer between two energy absorbing FRET components can be detected by a fluorimeter (e.g., a filter based or a monochromater based fluorimeter) that measures, for example, the ratio of fluorescence intensities at the two emission maxima wavelengths of the energy absorbing FRET components, or the quenching of the energy absorbing donor fluorescence at its emission maximum as a function of glucose concentration.

The first binding member can include a reduced valency CBL coupled to a first energy absorbing FRET component, and the second binding member can include a glycoconjugate that includes a carbohydrate and a second energy absorbing FRET component. The excited state energy levels of the first and second energy absorbing FRET components can overlap, and the reduced valency CBL and the glycoconjugate can reversibly bind one another (in which case, carbohydrate present in the sample would displace the glycoconjugate and reversibly bind to the reduced valency CBL). The extent or degree to which non-radiative fluorescence energy is transferred between the first and second energy absorbing FRET components can then be measured or monitored non-invasively.

As with methods carried out ex vivo, energy transfer can, for example, be evaluated by measuring one or more of: donor quenching, donor lifetime (e.g., a decrease in donor excited lifetime), sensitized acceptor emission, or fluorescence depolarization. It can also be measured by determining the ratio of two parameters, such as the ratio of: a donor parameter to an acceptor parameter (e.g., the ratio of donor to acceptor fluorescence, or depolarization of fluorescence relative to excitation); a donor parameter to a donor parameter (e.g., the ratio of donor to donor fluorescence, or depolarization of fluorescence relative to excitation); an acceptor parameter to an acceptor parameter (e.g., the ratio of acceptor to acceptor fluorescence, or depolarization of fluorescence relative to excitation).

Preferably, the sensor is positioned to evaluate a carbohydrate analyte (such as the monosaccharides, disaccharides, or polysaccharides described above) in the subject's subcutaneous body fluid, intracutaneous body fluid, or blood.

In another aspect, the invention features a sensor for non-invasively monitoring a carbohydrate (e.g., glucose) in a subject (i.e., the subject's skin does not have to be punctured each time a glucose level is obtained). Of course, the sensor can also be used to evaluate carbohydrates ex vivo (e.g., in a blood sample obtained from a subject). The sensor includes a specific binding pair that includes a first binding member and a second binding member, the first binding member including a reduced valency CBL coupled to a first energy absorbing FRET component, and the second binding member including a glycoconjugate that includes a carbohydrate and a second energy absorbing FRET component. The excited state energy levels of the first and second energy absorbing FRET components overlap and the reduced valency CBL and the glycoconjugate reversibly bind one another. Thus, carbohydrate present in the sample can displace the glycoconjugate and reversibly bind to the reduced valency CBL. Energy transfer can be evaluated as described above In vivo methods can be modified to provide positive feedback. For example, when glucose is monitored and found to be above an acceptable range, insulin can be administered (e.g., by an implanted pump) to lower the high level. In contrast, when glucose is below an acceptable range, a signal or alarm can be triggered to alert the subject (who can then ingest food or drink to raise the low level).

An energy absorbing FRET component, as used herein, is a substance that can either be a donor or an acceptor in the process of non-radiative energy transfer. Both the donor and the acceptor absorb energy. The function of the donor is to absorb energy at a first wavelength and transmit the absorbed energy via non-radiative energy transfer to the acceptor molecule. The function of the acceptor is to absorb the transmitted energy from the donor. The absorbed energy can be dissipated in a number of ways, for example, by emission of the energy at a second wavelength, dissipation as heat energy, or transfer of energy to the surroundings. Absorption by the acceptor can be measured by an acceptor parameter, e.g., sensitized acceptor emission or a donor parameter, e.g. donor fluorescence quenching. Requirements of the energy absorbing FRET components are that there is sufficient energy state overlap between the two in order for non-radiative energy transfer to occur. Furthermore, non-radiative energy transfer occurs only if the two are in close proximity (half energy transfer between a single donor and acceptor molecule occurs when the intermolecular distance is $R_0$.

An "energy absorbing FRET donor" is a substance that absorbs energy at a first wavelength. The absorbed energy creates an excited state in the donor. The donor can leave the excited state by emitting energy at an emission wavelength, by dissipating the energy in the form of heat, or by transmitting the absorbed energy via non-radiative energy transfer to an energy absorbing FRET acceptor. Accordingly, an "energy absorbing FRET acceptor" is a substance that absorbs the non-radiative energy transferred from the energy absorbing FRET donor. The absorbed energy creates an excited state in the acceptor, which the acceptor can leave by emitting the absorbed energy at a second wavelength, dissipating energy as heat, or transferring energy to its surroundings.

A first component "specifically binds" a second when the first component binds the second with a substantially higher affinity (e.g., with 50% greater affinity) than it binds a related component or moiety.

An interaction is "reversible" if it can proceed in either direction. A reversible reaction can consist, for example, of a forward reaction in which a glycoconjugate binds to a reduced valency CBL and a reverse reaction in which the glycoconjugate is released from the reduced valency CBL. Reversible reactions should occur under the conditions (e.g., physiological conditions) in which a carbohydrate is evaluated.

A carbohydrate is "evaluated" when it is detected in a sample (i.e., when one asks whether carbohydrate is present or absent) or quantitated in a sample.

A "subject" can be a human or other animal (e.g. a rodent, a dog, a pig, a cow, a sheep, a goat, or a non-human primate). The subject may have (or be suspected of having) a defect, e.g. a genetic or autoimmune defect, in carbohydrate metabolism. Thus, the methods and devices of the present invention can be used diagnostically.

A "physiological concentration" of a carbohydrate refers to the concentration of carbohydrate in a subject, who may be healthy or diseased (e.g., diabetic). For example, the physiological concentration of glucose includes the range of glucose concentrations found in normal, hypoglycemic, and hyperglycemic patients.

The methods and devices described herein can be used in clinical settings or other environments in which carbohydrate levels (e.g., glucose levels) are evaluated, as well as in the context of biomedical research. The devices can detect not only a broad range of glucose concentrations (e.g., from 0.05 mg/ml to 5.0 mg/ml or 0.5 mg/ml to 5.00 mg/ml) but also a wide range of other carbohydrate concentrations.

Furthermore, the methods and devices described herein can be non-invasive, and, as such, preclude rupturing a patient's skin regularly and thereby reduce the patient's risk of infection. This is particularly important for diabetic patients, who can have reduced resistance to infection.

In a sense, even implanted sensors are non-invasive, as they can be used repeatedly without regularly injuring the patient's skin. Because the components within the sensors do not aggregate and are not consumed, they are reliable and reusable for extended periods of time. Of course, the devices described herein can be used to measure many analytes other than glucose when they are configured, for example, to evaluate antibody-antigen interactions, receptor-ligand interactions, and enzyme-substrate interactions.

Other features and advantages of the invention will be apparent from the following detailed description, and from the claims.

DETAILED DESCRIPTION

Proximity Based Signal Generating Methods

Proximity methods include those in which a signal is generated when a first label on a first member of a specific binding pair is brought into close proximity with a second label on a second member of the specific binding pair. Examples of proximity methods include the following.

Fluorescence Resonance Energy Transfer (FRET)

Devices and methods for analyte detection can rely on FRET to determine the extent to which members of a specific binding pair (e.g., a glycoconjugate and a reduced valency CBL) bind one another in competition with a carbohydrate analyte. Both the reduced valency CBL and the glycoconjugate are coupled to a proximity based signal generating moiety (e.g., an energy absorbing FRET component). Interaction between the specific binding pair brings the two energy absorbing FRET components into the same vicinity where non-radiative energy transfer between them results in FRET. Because carbohydrate analyte in the sample competes with the glycoconjugate for binding to the reduced CBL, displacement of the glycoconjugate causes a decrease in FRET, which correlates with the concentration of the analyte.

When a molecule absorbs a photon of energy, it enters an excited state. To return to a resting state, this absorbed energy must be dissipated by radiative or non-radiative processes. Radiative processes involve the direct emission of light in the form of fluorescence (herein, "fluorescence" refers to both fast fluorescence and phosphorescence). In contrast, non-radiative processes allow exit from the excited state without direct emission of light by the donor. Non-radiative processes include dissipation of energy in the form of heat, use of the absorbed energy to promote chemical reactions, and transfer of energy to a neighboring molecule. The absorbing molecule enters an excited state and similarly eliminates the energy via radiative or non-radiative processes. Transfer of energy from one molecule to a second molecule occurs if there is sufficient energy state overlap and if the distance between the one energy absorbing donor and one energy absorbing acceptor is in the order of $R_0$.

Figure 1:
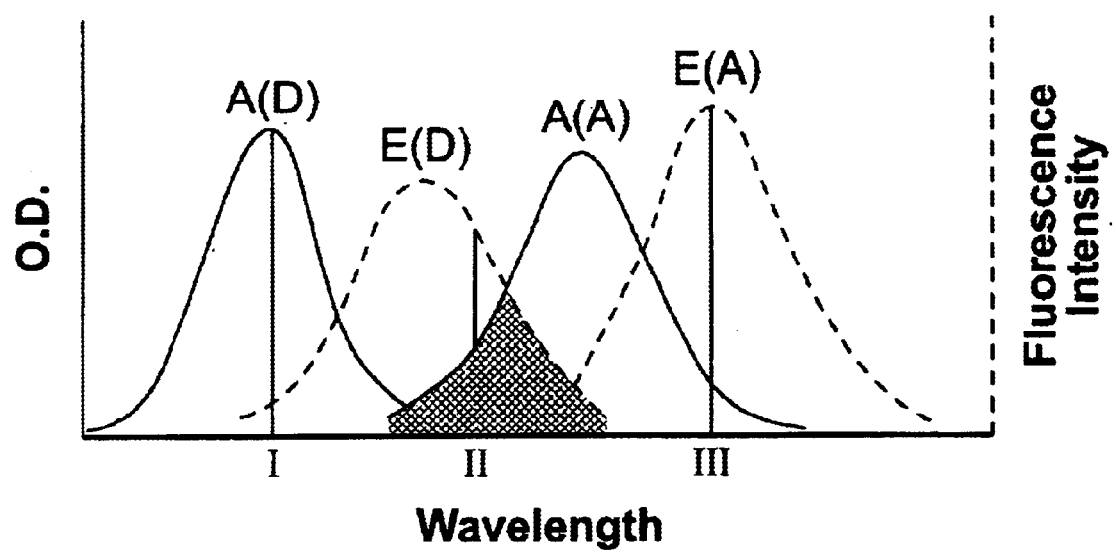
FIG. 1 is a graph demonstrating the absorbance and emission spectra of an energy absorbing donor and an energy absorbing acceptor.

FRET is represented diagramatically in FIG. 1. The absorbance and emission of the energy absorbing donor is designated A(D), and E(D), respectively, and the absorbance and emission of the energy absorbing acceptor is designated A(A) and E(A), respectively. The area of energy state overlap between the donor emission and the acceptor absorbance is important for energy transfer between the two components.

The process of FRET involves illuminating a sample at a wavelength that excites the energy absorbing donor but not the energy absorbing acceptor or that excites the energy absorbing donor to a much greater extent than it excites the energy absorbing acceptor. Excitation of the energy absorbing donor at wavelength I will result in energy being emitted at wavelength II, but not at wavelength III, the emission wavelength of the energy absorbing acceptor (see FIG. 1). Both the energy absorbing donor and the acceptor should absorb energy at one wavelength and emit energy at a different wavelength.

FRET is an all or nothing quantum mechanical event. Therefore, the energy from an individual energy absorbing donor is either transferred to an individual energy absorbing acceptor or it is not. Energy transfer only occurs when the absorption and emission spectra of the energy absorbing donor and energy absorbing acceptor overlap. When the energy absorbing acceptor (A) leaves its excited state, the emitted energy is rotated or depolarized with respect to the incident energy. As a result, FRET can be evidenced by a decrease in fluorescence intensity at II (i.e., decreased emission from the energy absorbing donor), an appearance of sensitized fluorescence intensity at III (i.e., an increased emission from the energy absorbing acceptor), or depolarization of the fluorescence relative to the incident energy.

FRET also manifests the lifetime in which the energy absorbing donor remains in an excited state. The number of molecules in an excited state are proportional to the rate at which molecules exit the excited state, plus the sum of radiative and non-radiative states. Fluorescence resulting from FRET is an equilibrium process, the duration of which depends on the time the energy absorbing FRET component remains in an excited state. This, in turn, is a result of competition between the rate at which the energy absorbing FRET component enters the excited state by the incident energy and the sum of the rates at which the energy absorbing FRET component leaves the excited state (by processes such as fluorescence and non-radiative energy transfer).

Figure 2:
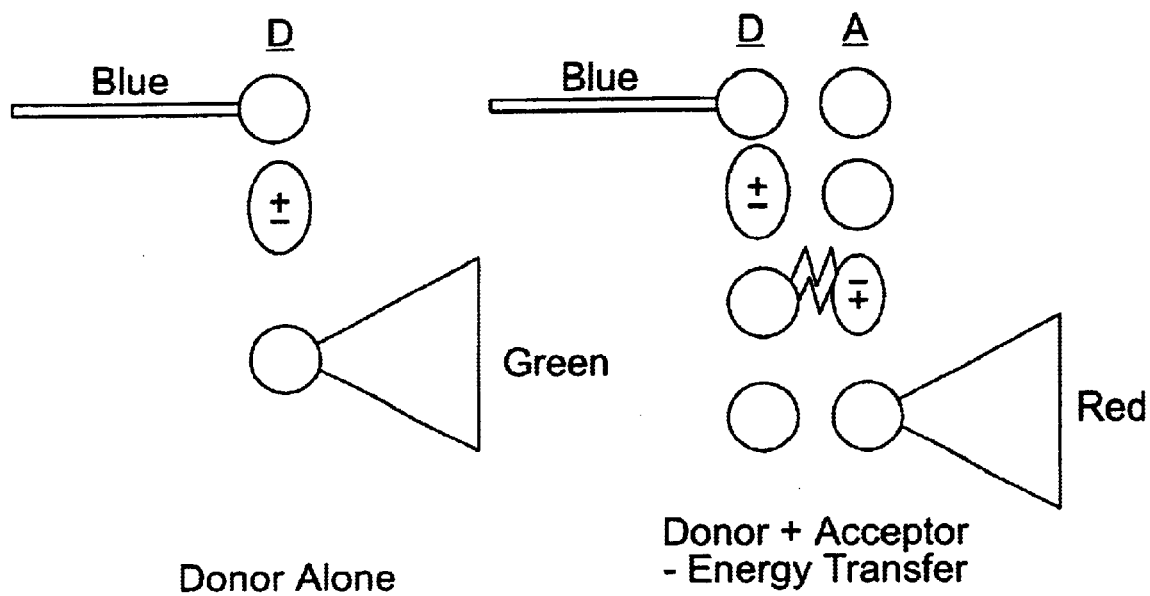
FIG. 2 is a schematic illustration of non-radiative energy transfer between two energy absorbing FRET components.

A common form of non-radiative energy transfer is transfer between singlet states. Non-radiative energy transfer between two energy absorbing FRET components in the same vicinity is shown in FIG. 2. An energy absorbing donor (D) absorbs a photon of energy that alters the charge distribution of the donor from a resting state to an excited state. The excited state charge distribution can be represented as a dipole where one side of the molecule becomes positively charged and the other side of the molecule becomes negatively charged. In addition to the emission of light, the energy absorbing donor molecule can return to its resting state by energy transfer from the energy absorbing donor to the energy absorbing acceptor (A), e.g., by inducing an opposite charged dipole in the energy absorbing acceptor molecule, which consequently enters an excited state. A requisite for energy transfer, for example, by dipole-induced dipole or energy transfer is that the energy absorbing acceptor is in the same vicinity as the energy absorbing donor. The energy absorbing acceptor can return to its resting state by emitting the absorbed energy at a different wavelength or non-radiative energy transfer.

As stated above, in a FRET-based evaluation of an analyte, a sample can be illuminated at a wavelength that excites the energy absorbing donor but not the energy absorbing acceptor, or that excites the energy absorbing donor to a much greater extent that it does the energy absorbing acceptor. The sample is usually monitored at two separate wavelengths: that of energy absorbing donor emission wavelength and that of energy absorbing acceptor emission wavelength. If the energy absorbing donor and energy absorbing acceptor are not sufficiently close, FRET occurs minimally and emission only occurs at the energy absorbing donor wavelength. If however, the energy absorbing donor and energy absorbing acceptor are sufficiently close, FRET occurs. The result of this interaction can be a decrease in energy absorbing donor lifetime, a quenching of energy absorbing donor fluorescence, and an enhancement of the energy absorbing acceptor fluorescence intensity. The efficiency of energy transfer $E_t$, for a single energy absorbing donor and a single energy absorbing acceptor, falls off rapidly as the distance between a single energy absorbing donor and a single energy absorbing acceptor molecule, R, increases, the relationship is represented by the following equation:

$$E_t = 1/[1+(R/R_o)6]$$

where R is the separation distance between energy absorbing donor and energy absorbing acceptor, and $R_o$ is the distance for half transfer. $R_o$ is a value that depends upon the overlap integral of the energy absorbing donor emission spectrum and the energy absorbing acceptor excitation spectrum, that index of refraction, the quantum yield of the donor, and the orientation of the donor emission and the acceptor absorbance moments (Forster, *Natuforsch.* 4A:321–327, 1949; Forster, *Disc. Faraday Soc.* 27:7–17, 1959).

Fluorescence can be detected by time resolved techniques, such as gating pulse method, pulse method, and phase modulation. In the gating pulse method, the sample is excited with a brief pulse of energy, and fluorescence is detected at a selected time period after the initial pulse. For example, if two fluorophores absorb energy and emit the absorbed energy in the form of fluorescence and one fluorophore has an fluorescence lifetime of 10 ns, while the second fluorophore has a fluorescence lifetime of 50 ns, it is possible to selectively detect the fluorescence from separate fluorophores. Detection at time 20 ns after the initial pulse of energy enables the detection of principally the fluorophore with the longer lifetime, i.e., the fluorophore with a fluorescence lifetime of 50 ns.

With the pulse method, the sample is excited with a brief pulse of energy and the time dependent decay of the fluorescence intensity is measured. For example, if the energy absorbing donor fluorescence decay is being measured, the rate of decay changes depending on energy transfer. If the energy absorbing donor transfers its energy to an energy absorbing acceptor via non-radiative energy transfer, the rate of the energy absorbing donor decay is faster than if the energy absorbing donor decays via radiative energy transfer.

Phase modulation is a method whereby the sample is excited with sinusoidal modulated energy and both the phase shift and amplitude of fluorescent light relative to the incident energy, is used to calculate the lifetime. For example, if the sample is excited with a light modulated sinusoidally at a specific frequency, due to the time lag between the absorption and emission, the emission is delayed in phase relative to the incident energy. This phase delay and amplitude modulation are used to calculate fluorescence lifetime.

Energy Absorbing FRET Components

An energy absorbing FRET component is a donor or an acceptor of non-radiative energy. Both donor and acceptor molecules absorb energy. The function of the donor molecule is to absorb energy at a first wavelength and transmit the absorbed energy via non-radiative energy transfer to the acceptor molecule. The function of the acceptor molecule is to absorb the transmitted energy from the donor molecule. Absorption allows for detection of energy transfer, e.g., by measurement of acceptor emission at a second wavelength. A requirement of the energy absorbing FRET components is that there is sufficient energy state overlap between the two molecules in order for non-radiative energy transfer to occur.

Preferred FRET components have the ability to absorb energy at a first wavelength and emit energy as fluorescence at a second wavelength. The FRET components should have energy state wavelengths in a range that avoid background interference from contaminants that may be present in the sample. Furthermore, the FRET components used in biological samples should have a fluorescence that is not quenched by water, since most biological measurements are made in an aqueous solution.

The relationship of energy absorbing donor and acceptor components is depicted in FIGS. 1 and 2. The energy absorbing donor absorbs energy at a first wavelength and enters an excited state. When the energy absorbing donor leaves the excited state, it can transmit the energy via non-radiative energy transfer. If there is sufficient energy state overlap with the energy absorbing acceptor, the energy can be transferred from the energy absorbing donor to the energy absorbing acceptor. Subsequently, the energy absorbing acceptor enters an excited state by absorbing the energy from the energy absorbing donor. Preferred energy absorbing acceptors emit energy in the form of fluorescent light which is rotated or depolarized with respect to the incident energy resulting in FRET upon leaving the excited state. The diagrammatic representation in FIG. 1 depicts FRET as a decrease in fluorescence intensity at II (i.e., decreased emission from the energy absorbing donor), an appearance of sensitized fluorescence intensity at III (i.e., an increased emission from the energy absorbing acceptor) and a depolarization of the fluorescence relative to the incident energy.

A FRET component is coupled to each member of a specific binding pair, e.g., to a reduced valency CBL and a glycoconjugate. The interaction between the specific binding pairs is responsible for bringing the two energy absorbing FRET donor and acceptor components together. Energy transfer will occur between the energy absorbing FRET donor and the energy absorbing FRET acceptor and FRET will be evidenced, e.g., in the form of decreased fluorescence intensity at II (i.e., decreased emission from the energy absorbing donor), an appearance of sensitized fluorescence intensity in III (i.e. increased emission from the energy absorbing acceptor) and depolarization of the fluorescence relative to the incident energy. In contrast, if there is no interaction between the specific binding pair will result in failure of the energy absorbing FRET donor and acceptor to come into sufficiently close proximity to allow efficient energy transfer. The presence of carbohydrate from a sample competes with the glycoconjugate for binding to the reduced valency CBL. Consequently, the binding site on the reduced valency CBL becomes occupied with the carbohydrate, preventing the glycoconjugate from binding and resulting in failure of FRET.

Suitable energy absorbing FRET components include fluorophores (e.g., NDB, dansyl, pyrene, anthracene, rhodamine, fluorescein and indocarbocyanine, and their derivatives). Dyes useful as energy absorbing FRET donor/acceptor pairs include indocarbocyanine⇌indocarbocyanine, (e.g., fluoresceino⇌rhodamine, NBD N-(7-nitrobenz-2-oxa-1,3-diazol-3-yl)⇌rhodamine, fluorescein⇌eosin, fluorescein⇌erythrosin, dansyl⇌rhodamine, acridine orange⇌rhodamine, pyrene⇌fluorescein, 7-amino-actinomycin-D⇌fluorescein, 7-aminoactinomycin-D⇌R-phycoerythrin, fluorescein⇌R-phycoerythrin, ethidium monoazide⇌fluorescein, and ethidium monoazide⇌R-phycoerythrin. Many of these dyes are commercially available or can be synthesized using methods known to those of ordinary skill in the art.

Energy absorbing FRET components may be tested for suitability as energy absorbing FRET donors or acceptors using the FRET system described in U.S. Pat. No. 5,342,789. For example, substances can be evaluated using glucose as an analyte, Concanavalin A as the ligand, and glucose conjugated to BSA as the glycoconjugate. The energy absorbing donor or the energy absorbing acceptor component may be coupled to either the glycoconjugate or the ligand. If the energy absorbing donor component is coupled to the glycoconjugate, then the energy absorbing acceptor component must be coupled to the ligand. If the energy absorbing acceptor component is coupled to the glycoconjugate, then the energy absorbing donor component must be coupled to the ligand. The occurrence of FRET will be indicative of energy state overlap and non-radiative energy transfer between the two components. The level of FRET resulting from a combination of a pair of components should correspond to the glucose concentration in the sample. This can be tested by exposing the pair of components to a series of samples containing known concentrations of glucose. The resulting FRET response should correspond to the concentration of glucose.

Homogeneous Time Resolved Fluorescence (HTRF)

Homogeneous time resolved fluorescence (HTRF) refers to a method of measuring constituents of a system without prior separation of those constituents. The basic concept of HTRF is based on FRET in that the interaction of two biomolecules (e.g., a glycoconjugate and a reduced valency are CBL each coupled to a proximity based signal generating moiety, e.g., to a donor and an acceptor fluorophore) can be measured by monitoring the fluorescence energy transfer from the excited donor fluorophore to the acceptor fluorophore when the two biomolecules are in proximity. The fluorescent signal from HTRF is measured after a time delay, thereby eliminating interfering signals.

Donor fluorophores useful in HTRF include rare earth chelates or cryptates e.g., terbium, europium, dysprosium, samarium or neodynmium, preferably europium cryptate [(Eu)k]. Suitable examples of acceptor fluorophores in HTRF include allophycocyanin (e.g., XL665), allophycocyanin B, phycocyanin C, phycocyanin R, and phthalocyanins.

The europium cryptate [(Eu)k] and XL665 FRET pair has several unique properties, for example, [(Eu)k] is stable within a pH range of 3 to 8 and has a long lifetime. This allows conventional equipment (such as a microplate fluorometer) to be used for measurement. Cryptate causes an enhancement of the $Eu^{3+}$ fluorophore, which subsequently transfers the energy to XL665 when the two components are in close proximity. Cryptate also functions to protect $Eu^{3+}$ from fluorescence quenching. The acceptor molecule in HTRF, namely XL665, is a stabilized allophycocyanin molecule that accepts energy transferred from [(Eu)k].

Luminescent Oxygen Channeling Assay (LOCI)

Luminescent oxygen channeling assay (LOCI) involves a photochemical reaction produced by the interaction of two proximity based signal generating label moiety components of the system. The first component, a photosensitizer, generates singlet oxygen upon irradiation (e.g., a phthalocyanine containing photosensitizer). The second component is a photochemically activatable chemiluminescent compound (e.g., olefin), which reacts with the singlet oxygen to initiate a delayed luminescence emission.

Photosensitizers produce singlet oxygen upon irradiation (e.g., light irradiation). Examples of photoactivatable photosensitizers include dyes and aromatic compounds. Examples of chemi-activated photosensitizers include enzymes and metal salts. The photosensitizers compound should absorb energy (e.g. light) in the wavelength range of 200–1100 nm, and the lifetime of the excited state produced must be sufficiently long to permit energy transfer to oxygen. Examples of photosenitizers are described in Turro, "Molecular Photochemistry," page 132, W. A. Benjamin, Inc., New York, N.Y., 1965.

Photochemically activatable chemiluminescent compounds that undergo chemical reaction upon direct excitation with light, or by reaction with singlet oxygen, form a metabstable reaction product that decomposes with emission of light, usually within the wavelength range of 250–1200 nm. Most photochemically activatable chemiluminescent compounds will usually emit at wavelengths above 300–550 nm.

Photochemically activatable chemiluminescent compounds that react with singlet oxygen include olefins (e.g., enol) ethers, enaminesdioxenes, arylimidazoles, luminol, luciferin, and aquaphorin.

Reduced Valency Carbohydrate Binding Ligands

A reduced valency CBL has the ability to bind, preferably reversibly, to a carbohydrate. The CBL should bind via a specific binding site (or sites) to the carbohydrate in a specific and reversible manner under the conditions that exist when measurements are to be made (e.g., physiological conditions). Valency refers to the number of carbohydrate binding sites, e.g., a valency of two refers to a species having two carbohydrate binding sites. Reduced valency CBLs refers to ligands which have been genetically engineered to have less than the normal valency.

For example, reduced valency CBLs can be subunits of a multimeric molecule, in which the subunit has been modified, e.g., by mutation, such that the subunit does not form the normal multimer (a genetically engineered ligand is a ligand having one or more alterations in its amino acid sequence). For example, a subunit of a multimer of four subunits can be modified such that subunits do not assemble into tetramers, but rather are present as monomers, dimers, or trimers. As is discussed elsewhere herein, Concanavalin A normally exists as a tetramer, formed from two associated dimers. The subunit encoding DNA can be mutagenized at residues important in monomer-monomer interactions to produce a monomer which does not assemble into dimers, or tetramers. The subunit encoding DNA can be mutagenized at residues important in dimer-dimer interactions to produce dimers which do not assemble into tetramers.

The reduced valency CBL should have as few carbohydrate binding sites as possible, preferably three or fewer and, preferably, a single carbohydrate binding site. For example, the reduced valency CBL can have a single carbohydrate binding site and be a monomeric molecule, e.g., a monomeric lectin molecule. If the reduced valency CBL is derived from a lectin or other naturally occurring molecule it will have at least one and preferably two fewer carbohydrate binding sites than the naturally occurring multimeric molecule.

The reduced valency CBL is one member of the specific binding pair and interacts with the carbohydrate coupled to the glycoconjugate, the second member of the specific binding pair. The reduced valency CBL is coupled to a proximity based signal generating label moiety (e.g., to an energy absorbing FRET component). The energy absorbing FRET component may either be a donor or an acceptor of energy. If the energy absorbing FRET donor is coupled to the reduced valency CBL, then the energy absorbing FRET acceptor is coupled to the glycoconjugate. If the energy absorbing FRET acceptor is coupled to the reduced valency CBL, then the energy absorbing FRET donor is coupled to the glycoconjugate.

Interaction between the reduced valency CBL and the glycoconjugate brings the energy absorbing FRET components together permitting non-radiative energy transfer and FRET. In the presence of carbohydrate in the sample, there is competition between the glycoconjugate and the carbohydrate for binding to the reduced valency CBL. As the binding site (or sites) on the reduced valency CBL becomes occupied by carbohydrate molecules, glycoconjugate molecules are displaced or prevented from binding. This prevents the energy absorbing FRET components from moving together and failure to promote the energy transfer between the components.

Examples of CBLs include a family of proteins called lectins. Lectins possess the ability to react reversibly with carbohydrates. The interaction is dependent on the lectin and the specificity of the lectin for particular carbohydrate moieties. Most lectins are oligomeric proteins, existing frequently as tetrameters or dimers. Examples of lectins are shown in Table I.

TABLE I

Characteristics of Lectins

| Lectin | Carbohydrate Binding Sites | Polypeptides | Molecular Weight |
|---|---|---|---|
| Canavalia ensiformis | 4 | 26,500 | 106,000 |
| Lathyrus satiuus | — | α 4,400β 19,000 | 49,000 |
| Lens culinaris | 2 | α 5,710 | 46,000 |

TABLE I-continued Characteristics of Lectins

| Lectin | Carbohydrate Binding Sites | Polypeptides | Molecular Weight |
|---|---|---|---|
| A | | β 17,572 | |
| | | α 5,700 | 46,000 |
| | | β 17,000 | |
| B | | | |
| Onobrychis viciifolia | — | α 26,509 | 53,000 |
| Pisum sativum A (I) | 2 | α 5,753 | 50,000 |
| | | β 17,000 | |
| | | α$^1$ 5,700 | 50,000 |
| | | β 17,000 | |
| B (II) | | | |
| Vicia cracca (Man) | 2 | α5,759 | 44,000 |
| | | β 17,500 | |
| Vicia ervilia | — | α4,700 | 53,000 |
| | | β 21,000 | |
| Vicia faba | 2 | α5,571 | 52,542 |
| | | β20,700 | |
| Vicia sativa | — | α 6,000 | 40,000 |
| | | β 14,000 | |
| Wistaria floribunda agglutinin | 1/chain | α 28,000–32,000 | (60,000)$_{1-4}$ |
| Wistaria floribunda mitogen | — | α 32,000 | 66,000 |

Preferred reduced valency CBLs are recombinant monomeric forms of multimeric proteins. In preferred embodiments a subunit of a multimeric protein is modified, e.g., by in vitro mutagenesis, to provide a molecule which is monomeric or which associates with fewer subunits than does the unmodified form. Reduced valency or monomeric Concanavalin A is particularly suitable. Site directed mutagenesis and recombinant technology can be used to produce reduced valency CBLs, for example, reduced valency Concanavalin A.

Naturally occurring Concanavalin A is composed of identical subunits which associate into a tetramer at physiological pH, and dissociates to yield dimers at a pH below 6.0, Wang et al., *J. Biol. Chem.* 250:1490–1502, 1975). Each monomeric subunit is approximately 27 kDa in mass and contains one carbohydrate binding site. Accordingly, tetrameric Concanavalin A is capable of binding four carbohydrate molecules.

Three-dimensional crystallographic studies of Concanavalin A have demonstrated that in dimeric Concanavalin A one monomeric subunit is paired across a two fold axis of symmetry with the second monomeric subunit, and that these dimers in turn are paired across 222 ($D_2$) points of symmetry to form tetramers (Becker et al., (1975), *J. Biol. Chem.* 250:1513–1524; Reeke et al., *J. Biol. Chem.* (1975), 250:1525–1546). These crystal structure of Concanavalin A can be used for rational design of modified or genetically Concanavalin A.

Interactions Involved in Dimeric Concanavalin A

Several types of interactions are involved in producing and stabilizing dimeric Concanavalin A (see Table II below) or tetrameric Concanavalin A (see Table III below). For example, Reeke et al., supra, describe residues from four distinct regions of the Concanavalin A structure that participate in forming contacts between monomeric subunits in dimeric Concanavalin A. Based upon this structure, the four regions include amino acid residues: 87–90, 136–139, and 175–178 (amino acid positions are by reference to the amino acid sequence data in Edelman et al., 1972, *Proc. Natl. Acad. Sci. U.S.A.*, 69:2580–4; Wang et al., 1975, *J. Biol. Chem.*, 250:1490–1502; and Cunningham et al., 1975, *J. Biol. Chem.*, 250:1503–12), which are located in the front of the monomeric Concanavalin A subunit. In contrast, amino acid residues 117–132 are located at the back of the monomeric Concanavalin A subunit.

Hydrogen bonding interactions involved in monomer-monomer interactions are described by Wang et al., supra. These include interaction between amino acid residues 125, 127, and 129 from one monomic Concanavalin A subunit which form a hydrogen bond with complementary amino acid residues of the second monomeric Concanavalin A subunit.

Other contacts also include van der Waals forces (VDWF) arising from amino acid residues 87, 90, 136–139 and 175–187 of a monomeric Concanavalin A subunit. Additional contacts arise through hydrophobic interactions between dimers involving amino acid residues 87, 88, 90, 117, 119 and 122–129.

Various interactions required in stabilizing dimeric Concanavalin A involve, for example, amino acid residues 125–132 from one monomeric Concanavalin A subunit interacting with amino acid residues 170–176 of the second monomeric Concanavalin A subunit (Hardman et al., *J. Biol. Chem.* 11:4910–4919, 1972).

TABLE II

Interactions Between Monomeric Subunits to Form Concanavalin A

| Residue | Interaction between monomers |
|---|---|
| 87 | VDWF |
| 88 | Hydrophobic |
| 90 | VDWF/hydrophobic |
| 117 | hydrophobic |
| 119 | hydrophobic |
| 125 | H-bond |
| 127 | H-bond |
| 129 | H-bond |
| 122–129 | hydrophobic |
| 136–139 | VDWF |
| 175–187 | VDWF |

Interactions Involved in Tetrameric Concanavalin A

Within tetrameric Concanavalin A, interactions between the four subunits are responsible for stabilizing the tetramer. For example, stabilization of tetrameric Concanavalin A via interactions arising from the side chains of amino acid residues projecting from each dimeric Concanavalin A subunit into the regions of dimer-dimer contact are described by Wang et al. supra. The most significant interaction between dimeric Concanavalin A subunits arises from four pairs of salt links between lysines 114 and 116 on one dimeric subunit and glutamic acid 192 on the other dimeric subunit. Additionally, histidyl residues 51 and 121 are within hydrogen bonding distances of serine 117 and serine 108, respectively, and may be linked to the latter by H-bonded solvent bridges. The amino acid residues involved in interactions between dimeric Concanavalin A subunits are summarized in Table III.

TABLE III

Interactions Between Dimeric Subunits to Form
Tetrameric Concanavalin A

| Residue | Interaction between dimers |
|---|---|
| 51 | H-bond |
| 108 | H-bond |
| 114 | Salt link |
| 116 | Salt link |
| 117 | H-bond |
| 121 | H-bond |
| 192 | Salt link |

Recombinant Production of Reduced Valency Concanavalin A

Table I and Table II provide amino acid residues which can be modified by site directed mutagenesis to generate modified Concanavalin A. Inactivation of residues in Table I can be used to produce Concanavalin A monomers, while inactivation of residues in Table II can be used to produce dimeric Concanavalin A.

Amino acid residues shown to be essential for interaction between Concanavalin A subunits can be modified by replacing the essential amino acid with another amino acid whose presence is shown to diminish subunit association. Site directed mutagenesis of nucleic acid encoding the Concanavalin A can be used to modify the structure of the Concanavalin A by methods known in the art. Such methods may, among others, include PCR mutagenesis (Ho et al., *Gene* 77:51–59, 1989).

Isolation of nucleic acid encoding Concanavalin A has been described in detail by Yamauchi et al. (*Eur. J. Biochem.* 170:515–520, 1988; *FEBS Letters* 260:127–130, 1990). Nucleic acid encoding the Concanavalin A polypeptide can be inserted into a suitable expression vector which is in turn used to transform a host cell to produce the polypeptide.

Expression vectors comprise a nucleic acid encoding Concanavalin A polypeptide in a form suitable for expression of the nucleic acid in a host cell. It will be appreciated by those skilled in the art that the design of the expression vector may depend on such factors as the choice of the host cell to be transformed, the level of expression of protein desired, etc. The expression vectors of the invention can be introduced into host cells to produce proteins or peptides, encoded by nucleic acids (e.g., Concanavalin A proteins, mutant forms of Concanavalin A proteins, and the like).

Various methods employed in the preparation of the expression vectors and transformation of host organisms are known in the art. Suitable expression vectors for both prokaryotic and eukaryotic cells, as well as general recombinant procedures are described in *Molecular Cloning A Laboratory Manual,* 2nd Ed., ed. by Sambrook, Fritsch and Maniatis (Cold Spring Harbor Laboratory Press: 1989) Chapters 16 and 17.

Host cells transfected to express a recombinant form of the Concanavalin A may be any prokaryotic (e.g. bacterial cells) or eukaryotic cell (e.g. yeast, avian, insect or mammalian). Procedures, or modifications thereof, can also be employed to prepare recombinant Concanavalin A by tissue-culture technology (e.g., in CHO cells or COS cells).

A host cell transfected with an expression vector directing the expression of Concanavalin A can be cultured under appropriate conditions to allow expression of Concanavalin A. The cells may be harvested, lysed, and the protein isolated. A cell culture includes host cells, media and other by-products. Suitable media for cell culture are well known in the art. Concanavalin A can be isolated from the cell culture medium, host cells, or both, by its affinity for maltose or glucose, or by standard methods for purifying proteins including ion-exchange chromatography, gel filtration chromatography, ultrafiltration, electrophoresis, and immunoaffinity purification with antibodies specific for Concanavalin A.

A variety of sequencing reactions known in the art can be used to directly sequence the Concanavalin A and detect mutations by comparing the sequence of the modified (mutated) Concanavalin A with the corresponding unmodified sequence. Exemplary sequencing reactions include those based on techniques developed by Maxam and Gilbert (*Proc. Natl. Acad. Sci. USA* 74:560, 1977) or Sanger (Sanger et al. *Proc. Natl. Acad. Sci. USA* 74:5463, 1977), or a variety of automated sequencing procedures may be utilized (*Biotechniques* 19:448, 1995).

Production of Reduced Valency Concanavalin in Plants

Transgenic plants e.g. monocotyledonous and dicotyledonous may also be used to produce monovalent Concanavalin A. In this case the DNA is inserted into the nuclear or plastidic genome. See, in general, *Methods in Enzymology* Vol. 153 ("Recombinant DNA Part D") 1987, Wu and Grossman Eds., Academic Press and European Patent Application EP 693554.

Foreign nucleic acid can be mechanically transferred by microinjection directly into plant cells by use of micropipettes. Foreign nucleic acid can be transferred into plant cell by using polyethylene glycol which forms a precipitation complex with the genetic material that is taken up by the cell (Paszkowski et al. *EMBO J.* 3:2712–2722, 1984).

Foreign nucleic acid can be introduced into a plant cell by electroporation (Fromm et al. *Proc. Natl. Acad. Sci. USA* 82:5824, 1985). In this technique, plant protoplasts are electroporated in the presence of plasmids or nucleic acids containing the relevant genetic construct. Electrical impulses of high field strength reversibly permeabilize biomembranes allowing the introduction of the plasmids. Electroporated plant protoplasts reform the cell wall, divide, and form a plant callus. Selection of the transformed plant cells with the transformed gene can be accomplished using phenotypic markers.

Cauliflower mosaic virus (CaMV) can also be used to introduce foreign nucleic acid into plant cells (Hohn et al. (1982) "Molecular Biology of Plant Tumors," Academic Press, New York, pp. 549–560; Howell, U.S. Pat. No. 4,407,956). CaMV viral DNA genome is inserted into a parent bacterial plasmid creating a recombinant DNA molecule which can be propagated in bacteria. After cloning, the recombinant plasmid again can be cloned and further modified by introduction of the desired DNA sequence into the unique restriction site of the linker. The modified viral portion of the recombinant plasmid is then excised from the parent bacterial plasmid, and used to inoculate the plant cells or plants.

Another method of introduction of foreign nucleic acid into plant cells is high velocity ballistic penetration by small particles with the nucleic acid either within the matrix of small beads or particles, or on the surface (Klein et al. *Nature* 327:70–73, 1987). Although typically only a single introduction of a new nucleic acid segment is required, this method particularly provides for multiple introductions.

A preferred method of introducing the nucleic acids into plant cells is to infect a plant cell, an explant, a meristem or a seed with *Agrobacterium tumefaciens* transformed with the nucleic acid. Under appropriate conditions known in the art, the transformed plant cells are grown to form shoots, roots, and develop further into plants. The nucleic acids can be introduced into appropriate plant cells, for example, by means of the Ti plasmid of *Agrobacterium tumefaciens*. The Ti plasmid is transmitted to plant cells upon infection by *Agrobacterium tumefaciens*, and is stably integrated into the plant genome (Horsch et al. *Science* 233:496–498, 1984; Fraley et al. *Proc. Natl. Acad. Sci. USA* 80:4803, 1983).

Ti plasmids contain two regions essential for the production of transformed cells. One of these, named transfer DNA (T DNA), induces tumor formation. The other, termed virulent region, is essential for the introduction of the T DNA into plants. The transfer DNA region, which transfers to the plant genome, can be increased in size by the insertion of the foreign nucleic acid sequence without affecting its transferring ability. By removing the tumor-causing genes so that they no longer interfere, the modified Ti plasmid can then be used as a vector for the transfer of the gene constructs of the invention into an appropriate plant cell.

There are presently at least three different ways to transform plant cells with *Agrobacterium:* (1) Co-cultivation of *Agrobacterium* with cultured isolated protoplasts; (2) transformation of cells or tissues with *Agrobacterium;* or (3) transformation of seeds, apices or meristems with *Agrobacterium*. The first method requires an established culture system that allows culturing protoplasts and plant regeneration from cultured protoplasts. The second method requires that the plant cells or tissues can be transformed by *Agrobacterium* and that the transformed cells or tissues can be induced to regenerate into whole plants. The third method requires micropropagation.

In the binary system, to have infection, two plasmids are needed: a T-DNA containing plasmid and a vir plasmid. Any one of a number of T-DNA containing plasmids can be used, the only requirement is that one be able to select independently for each of the two plasmids.

After transformation of the plant cell or plant, those plant cells or plants transformed by the Ti plasmid so that the desired DNA segment is integrated can be selected by an appropriate phenotypic marker. These phenotypic markers include, but are not limited to, antibiotic resistance, herbicide resistance or visual observation. Other phenotypic markers are known in the art and can be used in this invention.

Plants from which protoplasts can be isolated and cultured to give whole regenerated plants can be transformed so that whole plants are recovered which contain the transferred foreign gene. Some suitable plants include, for example, species from the genera *Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Hyoscyamus, Lycopersicon, Nicotiana, Solanum, Petunia, Digitalis, Majorana, Ciohorium, Helianthus, Lactuca, Bromus, Asparagus, Antirrhinum, Hererocallis, Nemesia, Pelargonium, Panicum, Pennisetum, Ranunculus, Senecio, Salpiglossis, Cucumis, Browaalia, Glycine, Lolium, Zea, Triticum, Sorghum,* and *Datura.*

Many plants can be regenerated from cultured cells or tissues. The term "regeneration" as used herein, means growing a whole plant from a plant cell, a group of plant cells, a plant part or a plant piece (e.g. from a protoplast, callus, or tissue part) (*Methods in Enzymology* Vol. 153 ("Recombinant DNA Part D") 1987, Wu and Grossman Eds., Academic Press; also *Methods in Enzymology,* Vol. 118; and Klee et al., (1987) *Annual Review of Plant Physiology,* 38:467–486).

Plant regeneration from cultural protoplasts is described in Evans et al., "Protoplasts Isolation and Culture," *Handbook of Plant Cell Cultures* 1:124–176 (MacMillan Publishing Co. New York 1983); M. R. Davey, "Recent Developments in the Culture and Regeneration of Plant Protoplasts," *Protoplasts* (1983)-Lecture Proceedings, pp. 12–29, (Birkhauser, Basal 1983); P. J. Dale, "Protoplast Culture and Plant Regeneration of Cereals and Other Recalcitrant Crops," *Protoplasts* (1983)-Lecture Proceedings, pp. 31–41, (Birkhauser, Basel 1983); and H. Binding, "Regeneration of Plants," *Plant Protoplasts,* pp. 21–73, (CRC Press, Boca Raton 1985).

Regeneration from protoplasts varies from species to species of plants, but generally a suspension of transformed protoplasts containing copies of the exogenous sequence is first generated. In certain species, embryo formation can then be induced from the protoplast suspension, to the stage of ripening and germination as natural embryos. The culture media can contain various amino acids and hormones, such as auxin and cytokinins. It can also be advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

In vegetatively propagated crops, the mature transgenic plants are propagated by the taking of cuttings or by tissue culture techniques to produce multiple identical plants for trialling, such as testing for production characteristics. Selection of a desirable transgenic plant is made and new varieties are obtained thereby, and propagated vegetatively for commercial sale. In seed propagated crops, the mature transgenic plants are self crossed to produce a homozygous inbred plant. The inbred plant produces seed containing the gene for the newly introduced foreign gene activity level. These seeds can be grown to produce plants that have the selected phenotype. The inbreds according to this invention can be used to develop new hybrids. In this method a selected inbred line is crossed with another inbred line to produce the hybrid.

Parts obtained from the regenerated plant, such as flowers, seeds, leaves, branches, fruit, and the like are covered by the invention, provided that these parts comprise cells which have been so transformed. Progeny and variants, and mutants of the regenerated plants are also included within the scope of this invention, provided that these parts comprise the introduced DNA sequences. Progeny and variants, and mutants of the regenerated plants are also included within the scope of this invention.

However, any additional attached vector sequences which confers resistance to degradation of the nucleic acid fragment to be introduced, which assists in the process of genomic integration or provides a means to easily select for those cells or plants which are transformed are advantageous and greatly decrease the difficulty of selecting useable transgenic plants or plant cells.

Selection of transgenic plants or plant cells is typically be based upon a visual assay, such as observing color changes (e.g., a white flower, variable pigment production, and uniform color pattern on flowers or irregular patterns), but can also involve biochemical assays of either enzyme activity or product quantitation. Transgenic plants or plant cells are grown into plants bearing the plant part of interest and the gene activities are monitored, such as by visual appearance (for flavonoid genes) or biochemical assays (Northern blots); Western blots; enzyme assays and flavonoid compound assays, including spectroscopy, see, Harborne et al. (Eds.), (1975) *The Flavonoids,* Vols. 1 and 2, Academic Press). Appropriate plants are selected and further evaluated. Methods for generation of genetically engineered plants are further described in U.S. Pat. Nos. 5,283,184, 5,482,852, and European Patent Application EP 693 554.

Screening Putative Reduced Valency Concanavalin A Species

Screening procedures to establish the production of a monomeric Concanavalin A include a heamagglutinin assay. The assay involves monitoring cross linking of red blood cells in the presence of monomeric Concanavalin A. Lack of red blood cell cross linking is indicative of a monomeric Concanavalin A species.

Further examples to determine the presence of a monomeric Concanavalin A species include standard non-reducing SDS-polyacrylamide gel electrophoresis, using techniques known to those skilled in the art. A molecular mass corresponding to the monomeric species, e.g. approximately 27 kDa is indicative of the monomeric species. Analytical procedures, for example, density gradient centrifugation, whereby the sample containing proteins or polypeptides of interest may also be used to determine the presence of monomeric Concanavalin A. The proteins or polypeptides are separated into discrete bands according to their molecular mass.

Mutant Concanavalin A can be tested for activity by virtue of its ability to bind a glycoprotein. In a relatively simple assay, in which the glycoprotein is bound to a substrate and the ability of the mutant Concanavalin A to bind to the substrate is evaluated. For example, glycoprotein can be bound to polymer beads and incorporated into a chromatography column. A solution containing mutant Concanavalin A can be applied to the column, the column is washed, and specifically bound mutant Concanavalin A is eluted with glycoprotein.

Mutant Concanavalin A can be tested for suitability as a reduced valency glucose binding ligand using the FRET system described in U.S. Pat. No. 5,342,789. For example, monomeric Concanavalin A can be evaluated using glucose as analyte and the sugar conjugated to BSA as the glycoconjugate. Proximity based signal generating label moieties e.g., energy absorbing FRET components such as the fluorescent dyes, BODIPY and fluorescein may be coupled to the specific binding pair. The occurrence of FRET is indicative of an interaction between Monomeric Concanavalin A and the glycoconjugate, resulting in the energy absorbing FRET components being brought into the close proximity and successful energy transfer.

Reduced valency Concanavalin A binding ligand has the distinct advantage and the ligand interacts with one molecule of analyte, preventing the problem of aggregation with multiple analyte molecules bound to Concanavalin A. This improves the sensitivity of the FRET system. Reduced valency recombinant Concanavalin A can be used for any reversible binding studies with improved sensitivities due to a single interaction at one binding site.

Reduced valency Concanavalin A has several advantages compared to the native Concanavalin A, e.g., reduced valency Concanavalin A minimizes aggregation associated with native Concanavalin A (in which the four molecules of carbohydrate bind to one molecule of Concanavalin A). Reduction of aggregation enables investigation of certain properties of Concanavalin A. For example, the ability of Concanavalin A to cross link receptors between two different cells leading to their agglutination.

Candidate reduced valency CBLs may be tested using the FRET system described in U.S. Pat. No. 5,342,789. For example, a candidate reduced valency CBL can be evaluated using a carbohydrate, e.g., glucose as analyte and the sugar conjugated to BSA as the glycoconjugate. Proximity based signal generating label moieties, for example, energy absorbing FRET components such as the fluorescent dyes rhodamine and fluorescein may be coupled to the specific binding pair. The occurrence of FRET is indicative of an interaction between the reduced valency CBL and the glycoconjugate, resulting in the energy absorbing FRET components being brought into the close proximity and successful energy transfer.

For accurate assessment of an interaction between the reduced valency CBL and the glycoconjugate, the carbohydrate conjugated on the glycoconjugate should be selected based on the specificity of the reduced valency CBL. For example to test the interaction of divalent succinyl-Concanavalin A as a reduced valency binding ligand, glucose or mannose should be the carbohydrate conjugated to the glycoconjugate, since Concanavalin A is known to have a high affinity for both. Therefore, suitable specific binding pairs which are useful not only for evaluating glucose but also have other implications for investigating the presence and concentration of other carbohydrates are disclosed herein.

Reduced valency ligands are advantageous in that a lower number of binding sites reduces aggregation. The glucose analyte need only compete with a minimal number of glycoconjugates from each reduced valency Concanavalin A. This improves the performance and sensitivity of the FRET system.

Glyconjugate

A glycoconjugate, as described herein, includes a carbohydrate, a label moiety, e.g., a FRET component a HTRF component, a LOCI component or other functionally similar substances and, preferably, a carrier molecule. The carbohydrate should be the same as the analyte. In FRET-based applications the label is a FRET component. In preferred embodiments the carbohydrate and the FRET component are both bound to a carrier molecule. The glycoconjugate binds specifically and reversibly to a reduced valency CBL.

A glycoconjugate is one member of the specific binding pair. It binds reversibly with:the reduced valency CBL, the second member of the specific binding pair. An energy absorbing FRET component is coupled to the glycoconjugate and can either be a donor or an acceptor of energy. If the energy absorbing FRET donor is coupled to the glycoconjugate, then the energy absorbing FRET acceptor is coupled to the reduced valency CBL. If the energy absorbing FRET acceptor is coupled to the conjugate, then the energy absorbing FRET donor is coupled to the reduced valency CBL.

The analyte carbohydrate should competitively inhibit binding of the glycoconjugate to the reduced valency CBL. Examples include carbohydrates such as glucose, fructose, sucrose, mannose, monosaccharides and oligosaccharides.

The carrier molecule (when present) should be nonreactive with substances found in the sample, provide a site at which a carbohydrate can be bound, and provide a site at which a FRET component can be bound. Furthermore, the carrier molecule should not interfere with the binding between the conjugated carbohydrate and the reduced valency CBL. Suitable carriers include proteins, such as bovine, or human serum albumin, β-lactoglobulin, immunoglobulins, antibodies, glycoproteins or glycolipids containing the carbohydrate moiety recognized by the reduced valency CBL; and synthetic polymers to which the carbohydrate is covalently coupled. Methods of coupling FRET components to carrier molecules are known to those skilled in the art and incorporated herein by reference (Hermanson, 1996, Bioconjugate Techniques, Academic Press, Inc).

A glycoconjugate can be tested for suitability using the FRET system described in U.S. Pat. No. 5,342,789. For example, a candidate glycoconjugate can be tested using glucose as the analyte and FRET labeled Concanavalin A as one member of the specific binding pair. Rhodamine and fluorescein can be used as the energy absorbing FRET components. Upon an interaction between the glycoconjugate and the Concanavalin A energy transfer between the energy absorbing FRET components will result in FRET. However, if there is no interaction between the glycoconjugate and the Concanavalin A, the energy absorbing FRET components will not be within a suitable distance for energy transfer and FRET will not occur.

FRET-based Measurement of Glucose Concentrations

Figure 3:
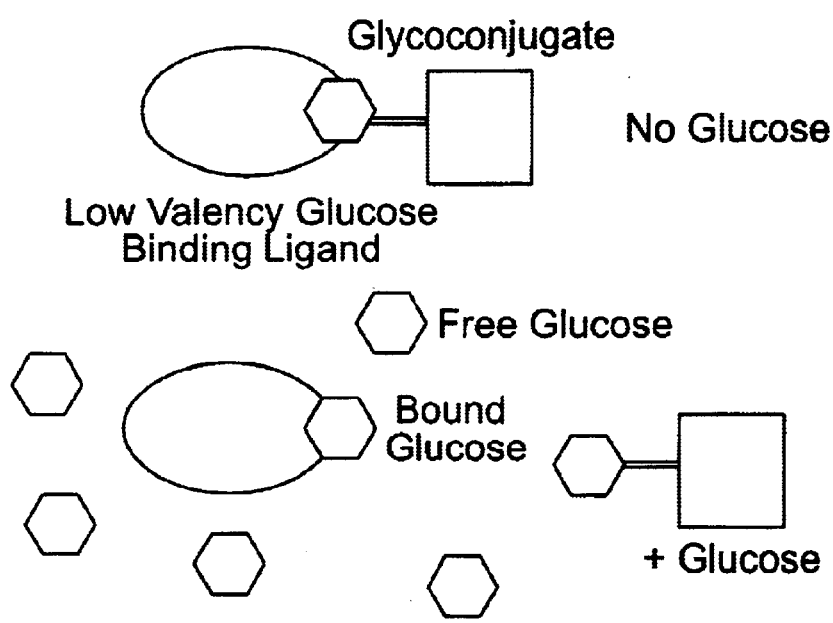
FIG. 3 is a schematic illustration of reversible binding between the specific binding pairs in the presence of glucose.

Glucose measurements using the reduced valency CBL and the glycoconjugate is based on reversible binding of the reduced valency CBL to free glucose or the glycoconjugate, as depicted in FIG. 3. In the absence of glucose, the glycoconjugate occupies the binding site on the reduced valency CBL. In the presence of glucose, the glycoconjugate is displaced and the binding site occupied by glucose.

Figure 4:
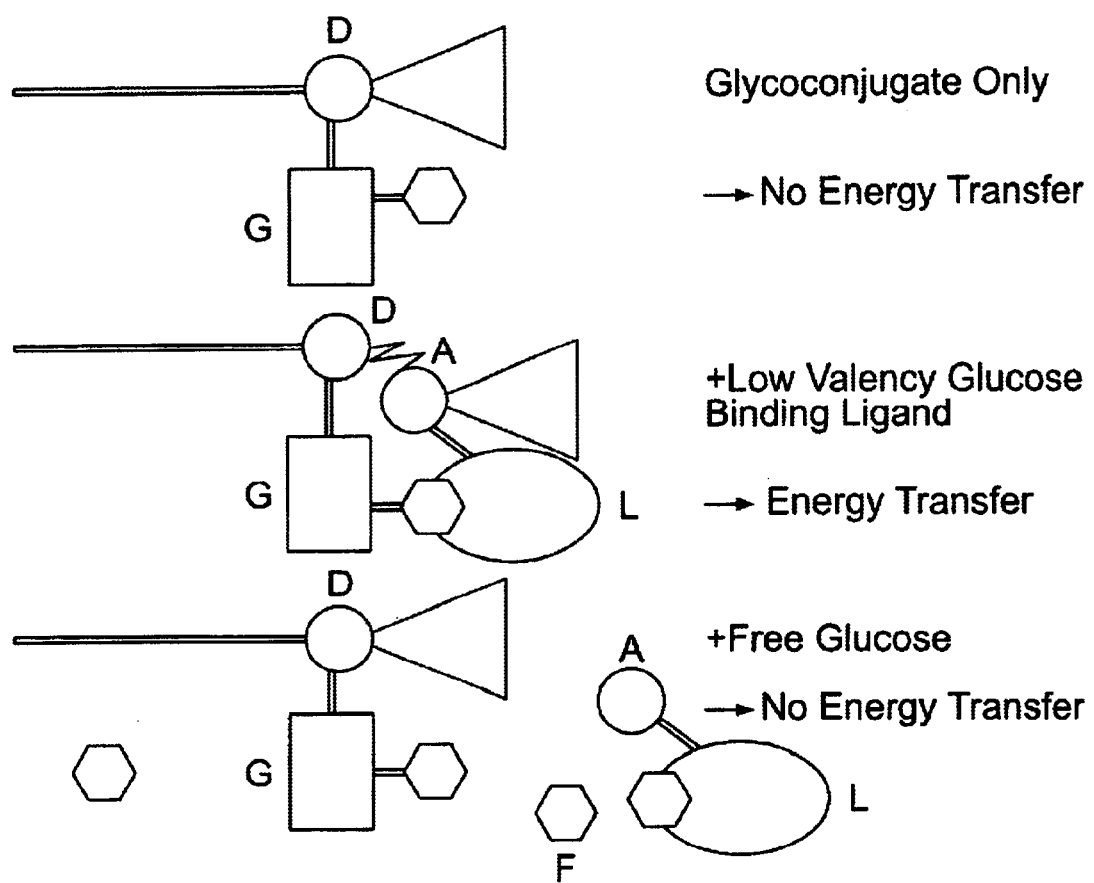
FIG. 4 is a schematic illustration of the use of FRET to evaluate glucose.

The use of FRET to measure glucose concentrations in solution is represented diagrammatically in FIG. 4. The specific binding pair includes a glycoconjugate (G) having glucose conjugated to a carrier molecule and having a covalently coupled energy absorbing FRET component, such as a fluororphore. The second binding member is a reduced valency glucose binding ligand (L) with a high specificity for glucose (e.g., reduced valency Concanavalin A, or reduced valency Concanavalin A derivatives), covalently coupled to an energy absorbing FRET component, such as a fluororphore. The energy absorbing FRET component on the glycoconjugate is generally not the same energy absorbing FRET component on the reduced valency glucose binding ligand.

One of the energy absorbing FRET component is an energy absorbing FRET donor (D) and the other an energy absorbing FRET acceptor (A). For the purposes of this illustration, the energy absorbing FRET donor (D) has been placed on the glycoconjugate (G) and the energy absorbing FRET acceptor (A) has been placed on the reduced valency glucose binding ligand (L). The association between the specific binding pair is shown below:

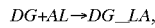

where DG represents the energy absorbing donor-glucose complex, AL represents the energy absorbing acceptor-reduced valency glucose binding ligand, and DG-LA represents the association between the glucose from the glycoconjugate and the reduced valency glucose binding. Upon association, the two members of the specific binding pair are close enough to allow energy transfer between the energy absorbing FRET donor and the energy absorbing FRET acceptor.

The presence of free glucose (F) introduces a competitive inhibitor into the formula because free glucose competes with the conjugated glucose for the reduced valency glucose binding ligand. The concentration of glucose has an inverse proportional relationship with the reduced valency glucose binding ligands available for glycoconjugate binding. Thus, increasing the glucose concentration decreases the number of reduced valency glucose binding ligands available for the glycoconjugate binding since the binding site (or sites) of the reduced valency glucose binding ligand become occupied with glucose. At relatively low concentrations of glucose, the non-radiative energy transfer efficiency between the energy absorbing FRET components will remain high because the interaction between the specific binding pairs is not significantly affected. In contrast, at high concentrations of glucose, the non-radiative energy transfer efficiency between the energy absorbing FRET components will be low, because glucose successfully competes the reduced valency glucose binding ligand away from the glycoconjugate. Thus it is possible to obtain a reliable, repeatable evaluation of glucose in a sample.

The methods of the invention are useful for evaluating glucose concentrations over a physiological range that includes that found in normal individuals, and those individuals with a glucose imbalance (i.e., patients with diabetes, hyperglycemia or hypoglycemia). The range of evaluation includes glucose concentrations from 0.05 mg/ml to 5.0 mg/ml or 0.5 mg/ml to 5.0 mg/ml. Measurements are made using an appropriate volume of sample from an individual (e.g., 10–100 μl), and the reactants are stable and reusable.

Various devices that are suitable for the detection of a carbohydrate, e.g., glucose concentration in blood either by in vivo or in vitro methods are within the invention. These devices can remain active for extended period of time (e.g., one, two, or six months or more) before having to be replaced.

In vivo embodiments provide for the cutaneous measurement of glucose by placing the reactants (i.e., the specific binding pair coupled to the energy absorbing FRET components) in contact with glucose. The reactants can be placed in, on, or under the skin. Alternatively, the reactants can be placed within an organ or a vessel (e.g., a vein or artery) where they are in exposed to the glucose in the body. In one embodiment, reactants are placed in, on or under the skin, and can, e.g., be monitored for glucose by illuminating the skin at a wavelength that excites the energy absorbing donor. The absorbed energy is transferred to an energy absorbing acceptor and FRET evaluated e.g., by measuring the emission maxima wavelength for the two energy absorbing FRET components. By way of example, if fluorescein and BODIPY are used as the energy absorbing FRET donor and the energy absorbing FRET acceptor, respectively, the fluorescent intensities are measured at 520 nm and 590 nm, $FI_{520}$ and $FI_{590}$, respectively (corresponding to the respective emission maxima wavelengths of these fluorescent dyes). The measure of energy transfer and the efficiency of energy transfer between the fluorescent dyes is detected by a fluorimeter. The ratio of fluorescence intensities at the two emission maxima wavelengths (e.g., $FI_{520}/FI_{590}$) or the quenching of the energy absorbing donor fluorescence (e.g., fluorescein) at its emission maximum as a function of glucose concentration is measured.

The reactants can be introduced into the body within a support material that retains the reactants at a desired location. For example, the reactants can be encapsulated in a microdialysis vessel or in microcapsules with a diameter of about 1 mm 50–100 mm. The encapsulated glucose sensor can be implanted intracutaneously in the body. In another procedure, reactants may be mixed with a carrier, e.g., silicone or fluorocarbon oils, and injected subcutaneously. The reactants may also be tattooed onto the skin or contained within a transcutaneous patch. Alternatively, the reactants may be modified in such a way that when injected subcutaneously, they become bound to cell structure and remain fixed in situ under the skin. For example, the albumin of the glycoconjugate can be engineered to include a reactive group that binds cells.

Any in vivo device that exposes the reactants to glucose can be modified to include an insulin pump. The pump can inject insulin into a patient upon detection of inappropriately high glucose levels.

In in vitro embodiments of the invention include exposing the reactants to a sample of blood or other bodily fluids containing glucose (e.g., urine, extracellular fluid) that has been removed from the body. Glucose is detected and quantified by exposing the reactants in with the glucose-containing bodily fluid in a fluorimeter.

In one embodiment, the reactants may be adhered to a solid substrate (e.g., a stick) or may be contained in a chamber (e.g., a microdialysis vessel). The reactants may also be contained in a pen cartridge that dispenses an appropriate volume of the reactants into the blood or other bodily substance containing glucose.

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. A method of evaluating a carbohydrate in a sample comprising:
   (a) contacting the sample with a specific binding pair that comprises:
      (i) a reduced valency carbohydrate binding ligand (CBL) and
      (ii) a glycoconjugate comprising a carbohydrate moiety, wherein the reduced valency CBL and glycoconjugate reversibly bind to each other; and
   (b) determining the extent to which the carbohydrate present in the sample displaces glycoconjugate bound to the reduced valency CBL and reversibly binds to the reduced valency CBL, the extent to which the carbohydrate binds to the reduced valency CBL being correlated with the amount of carbohydrate in the sample.

2. The method of claim 1, wherein the reduced valency CBL is a monomeric form of a multimeric protein.

3. The method of claim 1, wherein the reduced valency CBL is a lectin.

4. The method of claim 3, wherein the lectin is Concanavalin A.

5. The method of claim 4, wherein the Concanavalin A is mutagenized at residues that participate in dimer-dimer interactions to produce dimers which do not assemble into tetramers.

6. The method of claim 1, wherein at least one of the reduced valency CBL and the glycoconjugate include a detectable label.

7. The method of claim 6, wherein the label is a radioactive label, a fluorescent label, an enzyme, a proximity-based signal generating label moiety, a homogeneous time resolved fluorescence (HTRF) component, or a luminescent oxygen channeling assay (LOCI) component.

8. The method of claim 1, wherein the sample is a sample of urine, blood, plasma, saliva, intracellular fluid, interstitial fluid, homogenized cells, or a cell extract.

9. The method of claim 1, wherein the carbohydrate is a monosaccharide, a disaccharide, or a polysaccharide.

10. The method of claim 1, wherein the carbohydrate is glucose.

11. The method of claim 1, wherein the carbohydrate is a component of a glycoprotein.

12. The method of claim 1, wherein the glycoconjugate comprises serum albumin.

* * * * *